United States Patent [19]

Fruehwirth

[11] Patent Number: Plant 7,230

[45] Date of Patent: May 15, 1990

[54] POINSETTIA PLANT '8-84'

[75] Inventor: Franz Fruehwirth, Encinitas, Calif.

[73] Assignee: Paul Ecke Ranch, Inc., Encinitas, Calif.

[21] Appl. No.: 263,163

[22] Filed: Oct. 27, 1988

[51] Int. Cl.[5] ..... A01H 5/00

[52] U.S. Cl. ..... Plt./86

[58] Field of Search ..... Plt./86

*Primary Examiner*—James R. Feyrer

*Attorney, Agent, or Firm*—Arnold, White & Durkee

[57] ABSTRACT

The present invention describes a Poinsettia cultivar, designated '8-84', that is vigorous and self-branching, having a medium height with large, bicolored, red with pink-flecked flower bracts. '8-84' originated as a sport of the red bracted cultivar of plant U.S. Plant No. 5,492. '8-84' has self-branching traits which make it desirable for branched plant production, and can be flowered in a relatively cool greenhouse, making it economical to grow commercially.

1 Drawing Sheet

BACKGROUND OF THE INVENTION

'8-84' is a vigorous, self-branching Poinsettia of medium height and large bicolored, red with pink flecked flower bracts. It has self-branching traits which make it desirable for branched plant production. '8-84' can be flowered in a relatively cool greenhouse, making it economical to grow commercially.

This new Poinsettia cultivar originated as a sport of the red bracted cultivar of U.S. Plant No. 5,492 in a greenhouse in Encinitas, Calif. This pink on red sport has all the self-branching traits and other desirable growth characteristic of the cultivar of U.S. Plant No. 5,492. After selection, vegetatively reproduction of this plant by stem cuttings for test purposes in Encinitas, Calif., and clones of the plant were subjected to successive generations of vegetative propagation which demonstrated that its bract coloration and other distinctive characteristics hold true from generation to generation.

DESCRIPTION OF THE PHOTOGRAPHS

Poinsettia cultivar '8-84' of the invention is illustrated in the accompanying color photographs. The upper photo is a side view of typical unpinched plants in full flower. The lower photo is a top view of a plant showing flower and bract formation.

DESCRIPTION OF THE PLANT

The following is a detailed description of this new Poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of the cultivar of U.S. Plant No. 5,492.

Classification:

*Botanic.*—*Euphorbia pulcherrima* Willd.

*Common name.*—Poinsettia.

*Cultivar name.*—'8-84'.

Form: Shrub.

Height: Medium.

Growth habit: As a single stemmed plant, upright and vigorous. In full flower, the stem is terminated by a large inflorescence, with several smaller flowering side shoots lower on the stem. Observation of 3 plants in a pot with an overall height of 64 cm. and an overall width of 56 cm. were made. The bract diameter of individual flowers was 36 cm.

Branching: Branching can be enhanced by removal of the stem tip. Then, several flowering branches with equal vigor will develop on a single plant.

Growth rate: Very fast. Rooting of stem cuttings occurs in 12–18 days under intermittent mist. The plant will flower in about ten weeks under continuous long night conditions and night temperatures of about 16–8 degrees C.

Foliage: The foliage is clean and uniformly green from bottom to top of the plant. The leaves are of medium size, leaf blades typically being about 14–16 cm. long and about 9 cm. wide with leaf petioles about 7–8 cm. long.

Leaf shape: Typical leaves ae ovate with obtuse bases and acuminate tips. Leaf margins are mostly entire with some modest lobing and undulation.

Color:

*Upper side.*—Between RHS 147A an RHS 147B.

*Under side:*—Near RHS 137C.

Retention: The foliage retention is good even under low light intensities in the consumer's home.

Bracts: Generally there are 24–27 bracts of various sizes subtending the cyathia. The primary bracts have blades typically 14–16 cm. long and 10 cm. wide with petioles about 2–3 cm. long.

Shape: Bracts are mostly ovate with acute bases and acuminate tips. Primary bracts have som elobing and marginal indentations on either side of the bract.

Color:

*Upper side.*—Red with pink flecks and streaks. Red, between RHS 46A and RHS 46B. Pink, near RHS 51B.

*Under side.*—Red, near RHS 47A. Pink, near RHS 54C.

Cyathia: Generally, 15–18 cyathia (flowers) develop when the plant is in "full bloom". The type of inflorescence is a cyme, and each cyathium is subtended by a bract. Each cyathium is about 6–7 mm long and about 5–6 mm wide, green in color, and fringed with yellow at the distal end. Usually, two bright yellow nectar cups protrude from the side of each cyathium. The flower pedicel is also green and about 5–6 mm in length. The anthers protruding from the cyathia are red. The flowers appear to be nearly identical to those of the parent (U.S. Plant No. 5,492).

What is claimed is:

1. A new and distinct Poinsettia cultivar, substantially as herein shown and described, distinguished by its vigorous, self-branching characteristics, and large, bicolored, red with pink flecked flower bracts.

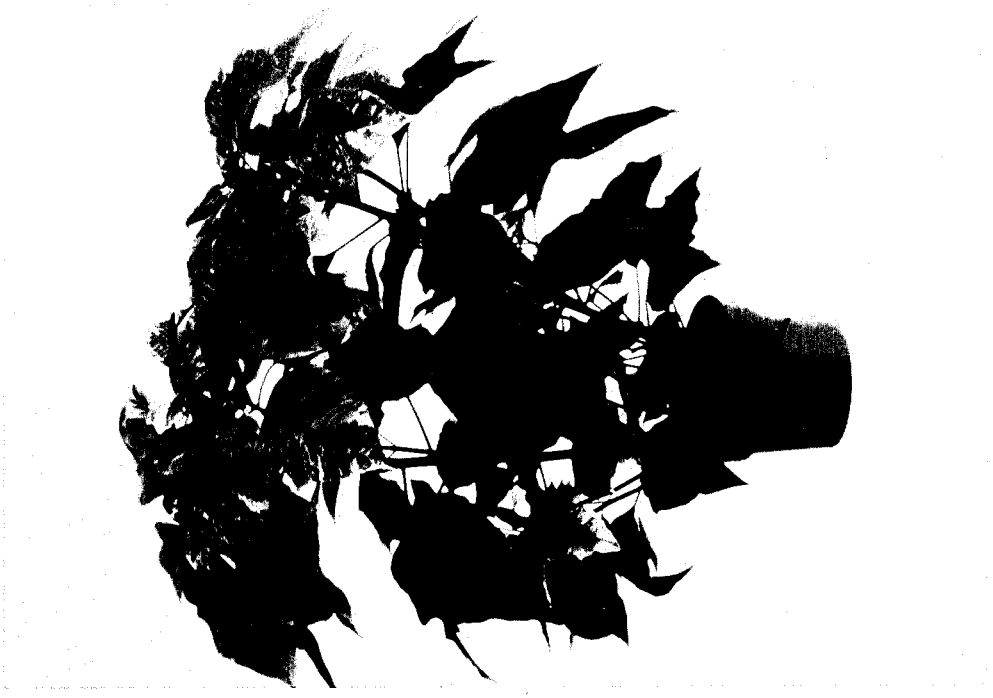
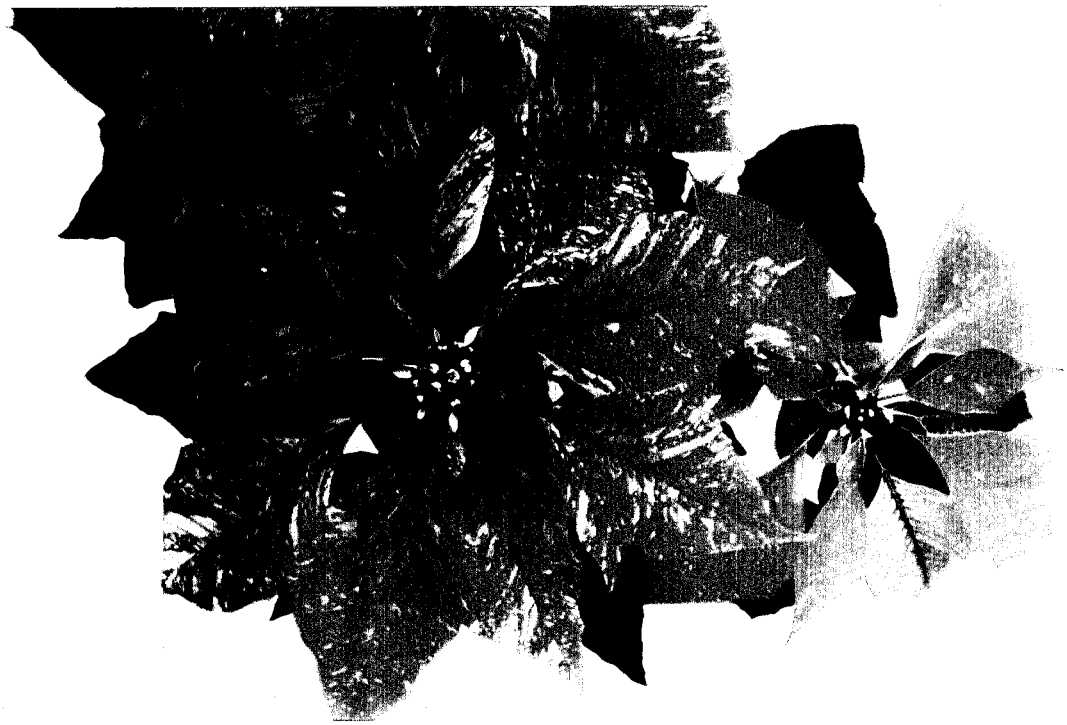

* * * * *